US005714467A

United States Patent [19]

Boman et al.

[11] Patent Number: 5,714,467

[45] Date of Patent: Feb. 3, 1998

[54] ANTIBACTERIAL AND ANTIMALARIAL HYBRID PEPTIDES

[75] Inventors: Hans G. Boman, Stockholm, Sweden; Robert B. Merrifield, Creskill, N.J.; David Andreu, Barcelona, Spain

[73] Assignee: The Rockefeller University, N.Y., N.Y.

[21] Appl. No.: 39,557

[22] Filed: Mar. 26, 1993

Related U.S. Application Data

[63] Continuation-in-part of Ser. No. 831,462, Feb. 5, 1992, abandoned, which is a continuation-in-part of Ser. No. 449,593, Dec. 12, 1989, abandoned, which is a continuation-in-part of Ser. No. 336,777, Apr. 12, 1989, abandoned.

[51] Int. Cl.$^6$ .................. A61K 38/16; C07K 7/00
[52] U.S. Cl. .................. 514/12; 514/21; 514/2; 530/324; 530/325; 930/20
[58] Field of Search .................. 514/12, 21, 2; 530/324, 325; 424/85.91; 930/20

[56] References Cited

PUBLICATIONS

Gwadz et al, Infection and Immunity, (Sep. 1989), vol. 57(9), pp. 2628–2633.
Christensen et al, Proc. Nat'l. Acad. Sci. USA, vol. 85, pp. 5072–5076, (Jul., 1988).
Roman et al, FEBS, vol. 259(1), pp. 103–106, (Dec. 1989).
Fink et al, Chem. Abs., vol. 111, 97703c; J. Biol. Chem. (1989), vol. 264 (11), pp. 6260–6267.
Boman et al, Chem. Abs., vol. 112(19), 175229m; FEBS Lett., vol. 259(1), pp. 103–106, (1989).
Li et al, FEBS Lett., vol. 231(2), pp. 299–302, (1988).
Boman, Chem. Abs., vol. 109(5), 36438g, (1986).
Jaynes et al, Chem. Abs., vol. 109(19), 165036y, (1988).
Jaynes et al, World Pat. 89–039653.
Kaslow et al, Chem. Abs., vol. 111, 224848f, (1989); Infect. Immun., vol. 57(9), pp. 2628–2633, (1989).
Kaaya et al, Chem. Abs., vol. 106(17), 136837t; Insect Biochemistry, vol. 17(2), pp. 309–315, (1987).
Degrado et al, J. Am. Chem. Soc 1981, 103, 679–681.

*Primary Examiner*—Ponnathapura Achutamurthy
*Assistant Examiner*—T. D. Wessendorf
*Attorney, Agent, or Firm*—Klauber & Jackson

[57] ABSTRACT

The invention relates to antibacterial and antimalarial peptides which are hybrids peptides which a of naturally occurring peptides such as cecropins, attacins, magainins, sarcotoxin, sapecin, bactenecins, alamethidicins, defensins and PGLa, and toxins such as streptolysins, melittin, barbatolysin, paradaxins and delta hemolysin. The hybrid peptides of the present invention are easily synthesized and have reduced toxicity. Also included in the invention are pharmaceutical compositions containing such hybrid peptides, and methods of treating patients infected with an organism against which these peptides are active.

22 Claims, 1 Drawing Sheet

FIG.1

ANTIBACTERIAL AND ANTIMALARIAL HYBRID PEPTIDES

This application is a continuation-in-part of U.S. application Ser. No. 07/831,462, filed Feb. 5, 1992 now abandoned which is, in turn, a continuation-in-part of application Ser. No. 07/449,593, filed Dec. 12, 1989 which is a continuation-in-part of U.S. application Ser. No. 07/336,777, filed Apr. 12, 1989. The last two applications are now abandoned.

BACKGROUND OF INVENTION

Several naturally occurring, antibiotically active peptides with useful therapeutic activity against pathogenic bacteria and other classes of microorganisms have recently been identified and isolated from insects, frogs and other animals. These include cecropins, attacins, magainins, sarcotoxin, sapecin, bactenecins, alamethicins, defensins and PGLa.

Other naturally occuring peptides from microorganisms, from insects and from higher animals are generally known as toxins because they lyse red blood cells as well as other eukaryotic cells. These toxins include different hemolysins such as streptolysins, melittin, barbatolysin, paradaxins and delta hemolysin. It is known, but it is not widely recognized, that some toxins like melittin will also kill bacteria. Therefore, for purposes of this description they will be described as antibiotically active peptides.

The invention described and claimed herein is based on the unexpected discovery that novel antibiotic molecules can be constructed by joining together at least two sequences from different antibiotics. One advantage of such hybrid molecules is that they may be constructed to be shorter and are, therefore, easier to synthesize than the natural peptides from which they are derived.

The hybrid peptides, in addition to their antibiotic activity, appear to have other features in common. For example, they generally contain about 15 to 40 amino acids and often they are more effective if their C-terminals are amidated or blocked in other ways. They are therefore potential candidates for commercial preparation by solid phase synthesis. Additionally, they all appear to contain certain sequences of amino acids which impart specific secondary characteristics to portions of the molecule. Often the N-terminus is hydrophilic and basic, and the C-terminus is hydrophobic. Some portions of the molecule have a tendency towards helicity, others do not. Some molecules contain relatively long sequences which are flexible, thus forming hinge regions in the molecule. Often the helical portions are amphipathic, i.e., they are characterized by a hydrophilic and a hydrophobic surface.

While we do not wish to be bound by theory, it appears that the antibiotics may function by rupturing the cell membrane of the bacteria or other organism. Binding of the peptides to the membrane permits entry of ions into the cellular fluid thus increasing the osmotic pressure and causing more fluid to enter the cell which increases the internal pressure and forces the cell to burst. The differing secondary characteristics of the different portions of the antibiotic peptides appear to be associated with their mode of action in piercing the cell membrane.

A very important current medical problem is to find antibiotics with enhanced potency against human pathogens especially those for which no suitable antibiotic is now available or to which resistant organisms have emerged by mutation of the original pathogenic organisms. One response to the emergence of organisms resistant to antibiotics has been to prepare synthetic derivatives of these compounds, but this approach has been limited by the availability of functional groups on the parent molecule that can be utilized as foci for preparing derivatives.

It would be useful if a pool of antibiotics of comparatively simple structure were available which could be prepared with relative ease and which at the same time would be susceptible to a variety of readily accomplished structural variations to produce synthetic antibiotically active peptides useful against specific organisms for which no non-toxic antibiotic is presently available, or of improved activity against other organisms for which the presently available antibiotics are toxic to the host. Such compounds should also have sufficient in vivo stability to resist degradation by mammalian enzymes.

It has been discovered that naturally occurring peptides such as those mentioned above, and others like them constitute such a pool.

THE INVENTION

Novel, antibiotically and/or antimalarially active, non-toxic peptides containing from about 15 to about 40 amino acid residues have now been discovered. These peptides are of improved pharmaceutical activity for any of a number of reasons. Some have improved activity against known pathogens. Some, unlike their naturally occurring counterparts are non-toxic and do not cause lysis of red blood cells. Still others are active against pathogens for which no completely satisfactory treatment is presently available.

The therapeutically useful peptides of this invention are characterized as hybrids containing at least one amino acid region containing from about 5 to about 20 amino acid residues in a sequence which is the same as or substantially similar to a corresponding segment on a natural antibiotic peptide, although variations in the length and sequence of the amino acid residues are possible.

This invention will be better understood by consideration of the application of the invention to cecropins and melittin.

The cecropins are a family of basic antibacterial peptides produced by the humoral immune response of certain insects as described in U.S. Pat. No. 4,355,104. Cecropins, together with attacins and lysozyme, are induced in the hemolymph of the pupae of the giant silk moth *Hylophora cecropia* following injection of live bacteria. There are three major cecropins, A, B and D. There is a high degree of homology between them, and all are of about the same size (cecropin A: 37 residues, cecropin B: 35 residues, cecropin D: 36 residues). They each contain a hydrophilic amino terminal chain and a hydrophobic amidated carboxyl terminus.

The amino acid sequences of cecropin A, B and D are shown in Table 1 which also includes the sequence of melittin. For convenience and ease of analysis the cecropin molecules have been divided into three sections: residues 1–11, 12–24 and 25 to the end. Those skilled in the art will recognize the high degree of homology and that cecropins A and B will be quite similar in their secondary structures. Both would be expected to have a strong potential in a polar environment to form an N-terminal amphipathic α-helix. The C-terminus will also have a tendency towards α-helix formation. In the central segment 12–24, there is some tendency for β-turns, for instance at residues 12–15, 15–18, 21–24. The N-terminus of cecropin D is less basic than either A or B. However, the central region of cecropin D has a higher potential for an α-helix than the A and B forms and also a strong preference for a helix in the C-terminal region.

In summary, the cecropins have a strongly hydrophilic amphipathic α-helix at the N-terminus, a more hydrophobic α-helix at the C-terminus, and a rather flexible, structurally less defined central region with some potential for β-turns.

The structure of melittin, an antibacterial peptide isolated from bee venom is shown in Table 1. It is a cationic amphipathic peptide in which residues 1–20 are predominantly hydrophobic and residues 21 to 26 are hydrophilic and basic. It will be noted that the major regions are arranged opposite from the cecropins. In melittin, they are hydrophobic/hydrophilic, and in the cecropins they are hydrophilic/hydrophobic. In the middle of the molecule there is a Gly-Leu-Pro region which may act as a hinge. Melittin has antibiotic activity, but is not useful for mammals because it is lytic for leukocytes, red blood cells and a wide variety of other cells.

It has now been discovered that it is possible to improve the pharmaceutical utility of naturally occurring, low molecular weight, antibiotically active peptides by rearranging selected regions or sequences of the peptides or, in some instances, adding a wholly new region to an intact region of a naturally occurring peptide. Thus a peptide formed by uniting the first 13 amino acid residues of cecropin A as the amino terminus with the first 13 amino acid residues of melittin; CA(1–13) M(1–13) has a lower lethal concentration and is more active against *Staphylococcus aureus* or *Bacillus subtilis* than cecropin A. Additionally, the novel 26-residue peptide is not lytic to sheep red blood cells even at concentrations greater than 200 μM. In contrast, melittin is lytic at 4–6 μM.

The term "improving the pharmaceutical activity" as used herein means that the novel peptide is less toxic to mammalian cells and/or more active against a spectrum of pathogens or against a specific pathogen than a naturally occurring peptide from which it is derived. A peptide of the invention is said to be "derived" from a naturally occurring peptide if it contains at least one region which is identical or substantially homologous to a region on a naturally occurring peptide. Thus CA(1–13) M(1–13) can be considered as derived from both cecropin A and melittin and is called a hybrid or chimeric peptide. Such products and their activity are novel and have not been previously described or suggested.

Other peptides within the scope of the invention may contain, for example, sequences from pig cecropin (PI), sarcotoxin, magainin, attacin, peptide PYL in one antibiotic. Typically, a hybrid peptide of the invention will contain a natural region from melittin or cecropin together with a wholly unnatural region designed to be more or less hydrophobic, hydrophilic, or helical than the "naturally occurring" sequence. Examples from each of these peptides have been synthesized and found to be active antibiotics.

It will be apparent to those skilled in the art that the selected region of the "naturally occurring" peptide in the final novel products of the invention does not need to be identical with the region in the natural peptide. One or more of the amino acid residues of the natural peptide may be replaced with another selected amino acid to increase the basicity, to interrupt the helicity or for any other useful reason. The sequence of amino acid residues in the novel product will, however, be substantially similar to the natural sequence. Typically, the degree of homology will be about 75% or more.

The peptides of the invention will normally contain from about 15 to about 40 amino acid residues. One reason is that antibiotically active low molecular weight peptides containing up to about 15 amino acids are normally not too difficult to synthesize. Another, is that peptides with more than about 40 amino acids are relatively difficult to synthesize in pure form by chemical synthesis, and may be best prepared by fermentation or by recombinant DNA procedures from the appropriate oligonucleotide. A particular advantage of the useful peptides of this invention is that they are readily synthesized by solid phase methods and a variety of combinations are possible to achieve specifically required results. An advantage of the use of solid phase techniques is that the product can be directly synthesized with the C-terminus amidated or otherwise blocked.

The term "region" as used herein is similar to "segment" or "fragment". It refers to amino acid sequences containing at least 5 and normally from about 5 to about 20 amino acids. A "region" is usually selected or constructed to be flexible, basic, hydrophobic, hydrophilic, amphipathic or helical, and that will be a characteristic of the region. A molecule may be constructed to have at least two regions and may or may not contain a hinge region. The region does not need to be derived from a naturally-occurring antibiotically active peptide containing 15 to 40 amino acid residues. It may be derived from a peptide containing less than 15 or more than 40 such residues.

The invention, then, comprises antibiotically and/or antimalarially active hybrid peptides and pharmaceutically acceptable salts thereof containing from about 15 to about 40 amino acid residues including at least one region with from 5 to 20 amino acid residues which is identical or substantially homologous to a corresponding sequence on a naturally occurring antibiotic and/or antimalarial peptide from which the novel peptide is derived for example, cecropin, melittin, magainin, attacin, sarcotoxin, $PYL^a$ or $PGL^a$. This selected region may be combined with one or more other regions of the same or another natural antibiotic and/or antimalarial peptide to form a hybrid molecule.

The invention also comprises pharmaceutical compositions containing such hybrid peptides or their pharmaceutically acceptable salts as well as methods of treating malaria and other microbial infections in mammals in need of such treatment by administration of an effective dose of said peptide or salt.

Typical compounds within the scope of this invention, all of which have been prepared and shown to have antibacterial activity may be represented by the following list wherein C represents cecropin, CA, CB and CD represent the A, B and D forms of cecropin, M represents melittin and Mag represents magainin. The numbers represent the sequence of amino acid residues in the corresponding region of the natural peptide. The notations define the characteristics of the region CA(1–13)Mag(13–23) - hydrophilic/hydrophobic
M(15–26)Mag(13–23) - hydrophilic/hydrophobic
Mag(13–23)CA(1–13) - hydrophobic/hydrophilic
Mag(13–23)M(15–26) - hydrophobic/hydrophilic
M(1–13)CB(1–13) - hydrophobic/hydrophilic
M(1–12)ProCA(1–13) - hydrophobic-Pro-hydrophilic
M(1–15)C(1–11) - hydrophobic/hydrophilic
M(16–26)CA(14–37) - hydrophilic/hydrophobic
CA(25–36)ProCA(1–13) - hydrophobic-Pro-hydrophilic
CA(25–37)CA(1–13) - hydrophobic/hydrophilic
CA(1–24)M(1–13) - hydrophilic/hydrophobic
CA(1–13)M(1–13) - hydrophobic/hydrophilic
M(16–26)M(1–13) - hydrophilic/hydrophobic M(16–26)CA(23–37) - hydrophilic/hydrophobic
CA(1–24)M(16–26) - hydrophilic/hydrophilic
CB(25–35)M(14–26) - hydrophobic/hydrophilic
CA(1–17)CD(12–37) - hydrophilic/hydrophobic
CA(1–8)M(1–18) - hydrophilic/hydrophobic
CA(1–9)M(1–17) - hydrophilic/hydrophobic
CB(1–13)M(1–13) - hydrophilic/hydrophobic
CA(1–17)M(1–9) - hydrophilic/hydrophobic
CA(1–18)M(1–8) - hydrophilic/hydrophobic
M(1–13)CA(1–22) - hydrophobic/hydrophilic
M(1–13)CA(1–13) - hydrophobic/hydrophilic
CA(1–8)M(1–12) - hydrophobic/hydrophilic
CA(1–8)M(1–10) - hydrophobic/hydrophilic
CA(1–7)M(1–8) - hydrophobic/hydrophilic
CA(1–7)M(2–9) - hydrophobic/hydrophilic
CA(1–7)M(3–10) - hydrophobic/hydrophilic
CA(1–7)M(4–11) - hydrophobic/hydrophilic
CA(1–7)M(5–12) - hydrophobic/hydrophilic
CA(1–7)M(6–13) - hydrophobic/hydrophilic The preferred compounds, based on scope and degree of activity, are CA(1–13)M(1–13), CA(1–8)M(1–18) and CA(1–7)M(2–9).

Most of the above products, in addition to being hydrophobic/hydrophilic or vice-versa will also have regions of helicity or amphipathicity. Proline (Pro) is often employed to interrupt a helix although other amino acids may be similarly employed. The above peptides can also be constructed to include a flexible or hinge region.

The presently preferred peptides within the scope of this invention will include regions containing about 7 to 20 amino acid residues wherein the regions are substantially homologous to a corresponding region from a cecropin, melittin, magainin or attacin.

A particularly preferred antibiotic of this invention is Gly-Ile-Gly-Lys-Phe-Leu-Lys-Lys-Ala-Lys-Lys-Gly-Ile-Gly-Ala-Val-Leu-Lys-Val-Leu-Thr-Thr-Gly-Leu (SEQ ID NO: 1). This compound is a hybrid of the first eleven amino acid residues of magainin and residues 12 to 24 of melittin except that residues 7 and 8 of the antibiotic are both lysines whereas the analogous residues in magainin are histidine and serine. It is a typical example of compounds within the scope of the invention in which a region of the antibiotic is homologous to a region on the natural product.

The compounds of this invention may be chemically synthesized by standard solid phase procedures using the protection, deprotection and cleavage techniques and reagents appropriate to each specific amino acid or peptide. A combination of manual and automated (e.g., APPLIED BIOSYSTEM® 430A) solid phase techniques can be used to synthesize the novel peptides of this invention. For background on solid phase techniques, reference is made to Andreu, D., Merrifield, R. B., Steiner, H. and Boman, H. G., (1983) Proc. Natl. Acad. Sci USA 80, 6475–6479; Andreu, D., Merrifield, R. B., Steiner, H. and Boman, H. G., (1985) Biochemistry 24, 1683–1688; Fink, J., Boman, A., Boman, H. G., and Merrifield, R. B., (June 1989) Int. J. Peptide Protein Res. 33, 412–421; Fink, J., Merrifield, R. B., Boman, A. and Boman, H. G., (1989) J. Biol. Chem. 264, 6260–6267; each of which being hereby incorporated herein by reference.

The in vivo stability of the compounds of the invention can be improved by adding a D-amino acid to the N- and C-termini. This procedure is particularly useful with products of the invention which are employed under conditions, parenteral or oral, where they will be subject to hydrolysis by naturally occurring enzymes before they perform their desired physiological function.

Since the products of the invention are amphoteric they may be utilized as free bases, as acid addition salts or as metal salts. The salts must, of course, be pharmaceutically acceptable, and these will include metal salts particularly alkali and alkaline earth metal salts, suitably potassium or sodium salts. A wide variety of pharmaceutically acceptable acid addition salts are available. These include those prepared from both organic and inorganic acids, preferably mineral acids. Typical acids which may be mentioned by way of example include citric, succinic, lactic, hydrochloric and hydrobromic acids. Such products are readily prepared by procedures well known to those skilled in the art.

A further aspect of the present invention provides pharmaceutical compositions which comprise one or more compounds of the invention and a pharmaceutically acceptable carrier. The compositions may be made up in any pharmaceutical form appropriate for the desired route of administration. Examples of such compositions include solid compositions for oral administration such as tablets, capsules, pills, powders and granules which may be enteric coated or otherwise protected from hydrolysis, especially enzymatic hydrolysis. Liquid compositions for oral administration such as solutions, suspensions, syrups or elixirs and preparations for parenteral administration such as sterile solutions, suspensions or emulsions. The compositions may also be manufactured in the form of sterile solid compositions which can be dissolved in sterile water, physiological saline or some other sterile injectable medium immediately before use. Topical compositions, typically in the form of emulsions, suspensions, creams, lotions or foams which may contain emollients, suspending agents, chelating agents, stiffening agents, buffering agents, and other components conventionally used with topical compositions containing antibiotics may also be provided.

In all such compositions, the antibiotic and/or antimalarial will normally be the principal physiologically active ingredient.

Optimal dosages and regimens for a given mammalian host can be readily ascertained by those skilled in the art. It will, of course, be appreciated that the actual dose used will vary according to the particular composition formulated, the particular compound used, the mode of application and the particular site, host and disease being treated. Many factors that modify the action of the drug will be taken into account including age, weight, sex, diet, time of administration, route of administration, rate of excretion, condition of the patient, drug combinations, reaction sensitivities and severity of the disease.

The following non-limiting examples are given by way of illustration only and are not to be considered limitations of this invention, many apparent variations of which are possible without departing from the spirit or scope thereof. The examples illustrate the in vitro activity of the compounds of this invention against a variety of infectious organisms. They are illustrative of the studies which the art has relied on for close to half a century as reasonably predictative of the efficacy of compounds, particularly antibiotics for treatment of mammalian infections.

EXAMPLES

EXAMPLES 1–6 AND COMPARISON WITH CA (1–37), CD(2–37), AND M(1–26)

Novel peptides of this invention and melittin were synthesized by a combination of automated (Applied Biosystem 430A) solid phase techniques (see articles regarding synthesis, cited supra). In particular, melittin and the novel peptides CA(25–37)CA(1–13), M(1–13)CA(1–13), CA(1–11)CD(12–37) , CA(1–24)M(1–13) , CA(1–13)M (1–13), and M(16–26)M(1–13) were prepared by the following standard double coupling protocol, based on 2.5 g of starting resin (0.21 mmol/g): (1) $CH_2Cl_2$, 50 mL, 4×1 min; (2) 50% TFA/$CH_2Cl_2$, 50 mL, 2×1 min; (3) 50% TFA/ $CH_2Cl_2$, 50 mL, 1×20 min; (4) $CH_2Cl_2$, 50 mL, 6×1 min; (5) 5% DIEA/$CH_2Cl_2$, 50 mL, 2×2 min; (6) $CH_2Cl_2$, 50 mL, 6×1 min; (7) protected amino acid, 4 eq in 20 mL of $CH_2Cl_2$, add to reaction vessel, rinse with 4 mL of $CH_2Cl_2$, and shake at room temperature for 5 min; 4 eq of DCC in 3 mL of $CH_2Cl_2$, add to reaction vessel, rinse with 2 mL of $CH_2Cl_2$ and shake for 100 min at room temperature; (8) $CH_2Cl_2$, 50 mL, 4×1 min; (9) 5% DIEA/$CH_2Cl_2$, 50 mL 1×2 min; (10) $CH_2Cl_2$, 50 mL, 4×1 min; (11) DMF, 50 mL, 2×2 min; (12) protected amino acid, 8 eq in 3 mL of $CH_2Cl_2$, 0° C., add DCC, 4 eq in 1 mL of $CH_2Cl_2$, 0° C., rinse with 1 mL of $CH_2I_2$, 0° C., after 10 min. at 0° C., filter, add 25 mL of DMF, 0° C., add to reaction vessel, rinse with 5 mL of DMF, 0° C., shake for 1 h at room temperature; (13) DMF, 50 mL, 2×2 min; (14) $CH_2Cl_2$, 50 mL, 4×1 min; (15) 5% DIEA/ $CH_2Cl_2$, 50 mL, 1×2 min; (16) $CH_2Cl_2$, 50 mL, 4×1 min; (17) 3- to 5-mg sample for ninhydrin analysis. This protocol is repeated for subsequent amino acids to complete the assembly of the desired peptide.

The fully protected peptide on the resin is then treated with TFA to remove the N Boc group and dried. Cleavage of the peptide from the resin supports is accomplished by the low/high HF method, Tam et al (1983) *J. Am. Chem. Soc.* 105 6442–6455. Low HF is accomplished with 5 mL of HF/dimethyl sulfide/p-cresol/p-thiocresol (25:65:7.5:2.5), at 0° C. for 2 hr. High HF is accomplished with 10 mL of HF/p-cresol/p-thiocresol (95:3.75:1.25), at 0° C. for 1 hr. After evaporation of HF, the product is first washed with anhydrous ether to remove the scavengers, and then dissolved in 10% HOAc in water. The crude material is obtained by lyophilization.

The peptides of the invention are then partially purified by gel filtration on a SEPHADEX® G25 polysaccharide dextran column in 1M HOAc to remove low molecular weight impurities. After lyophilization the products are normally obtained in a yield of about 80%, based on the first amino acid. Reverse phase, low pressure, preparative liquid chromatography on a VYDAC® C18 reverse phase chromatographic column column (218TPB10) and elution with linear gradient of 25–65% acetonitrile, in certain instances, followed the SEPHADEX® polysaccharide dextran gel filtration.

The synthesis of the peptides of this invention is not limited to the solid phase method described. They may be synthesized by other methods known to the skilled artisan including recombinant technology procedures.

The products of the invention were tested for activity against a variety of test organisms selected to represent a number of different types of pathogens some of them known to be particularly virulent by the inhibition zone assay of Hoffmann et al (1981) *Insect Biochem.* 11 537–548 which is incorporated herein by reference. Thin agar or agarose plates (8.5 cm diameter) were prepared with 6 ml of rich medium containing 100 ug/ml of streptomycin and $2\times10^5$ viable cells of a test organism resistant to streptomycin. Wells of 35 mm diameter were punched in the plates and 3 ul of serially diluted samples were placed in the wells. The diameters of the zones of inhibition around the wells were measured after overnight incubation at 30° or 37° C. For each peptide the squares of the zone diameters were plotted against the logarithm of the concentration, and from the slopes and intercepts the lethal concentrations were calculated as described by Hultmark (1983) EMBO J. 2, 571–76 or Hultmark et al (1982) *Eur. J. Biochem.* 127 207–217 each of which being incorporated herein by reference. The results of the assays with some of the products of the invention are shown in Table 2.

The Table 2 also shows the concentrations at which the compounds will lyse sheep red blood cells. These values were obtained by either the lysis assay normally used for melittin or by an adaptation of the antibacterial inhibition zone assay of the above-cited Hultmark et al articles to plates with sheep red cells (SRC). With respect to the latter, sterile agarose plates contained 6 ml of medium With 1% agarose, 0.9% NaCl and 10% SRC suspended in Alsevers solution. A dilution series of peptide was applied in 3 mm wells each loaded with 3 µl of the respective samples. The plates were incubated at 30° C. for 24 h, the zones were recorded and LC values calculated as described in the Hultmark et al articles. Clear zones were recorded after a few hours of incubation and the use of such data gave an LC value of the same order as readings after 24 h. This plate assay is faster and more convenient than the lysis assay normally used for melittin.

Assays for the minimum inhibitory concentration of the products of the invention were conducted according to standard bacteriological procedures. These tests assisted in establishing the antibacterial utility of the products.

It was observed during testing that basic peptides often bind to agar plates, but not so much to agarose. Therefore those lethal concentrations determined on agar may, in fact, be substantially higher than the actual lethal concentrations.

It will be seen that all of the hybrid peptides are less toxic than melittin as measured by ability to lyse sheep red blood cells. It will be seen also that against specific organisms most of them are more active than at least one of the naturally occurring peptides from which it is derived. CA(1–11)CD (12–37) is more active than either cecropin A or cecropin D against the organisms tested. The most profound increases in antibiotic activity were with CA(1–13)M(1–13) and CA(1–24)M(1–13) against *Staphylococcus aureus* and *Bacillus subtilis* where increases of 40 to 200 fold over cecropin A were observed. The potency of these two hybrid peptides against a yeast *Sacchromyces cerevisiae* was also greater than cecropin A. Furthermore, these two compounds were not toxic to sheep red blood cells even at 100 µM and higher.

They were also much more active against the malarial parasite than CA or M.

One interesting embodiment of this invention is the hybrid M(16–26)M(1–13) in which the two principal regions of melittin are reversed. This product did not lyse red cells even at 240 µM, whereas the natural melittin molecule caused lysis at 4–6 µM, a greater than 40–60 fold improvement.

EXAMPLES 7–8 AND COMPARISON WITH Mag, CB, CA AND PGLa

Hybrid peptides CA(1–13)M(1–13) and CA(1–8)M (1–18) were prepared as described above (see Examples 1–6) and were assayed for activity against the blood stream form of *Plasmodium falciparium*. For comparison the test included cecropins A and B and the frog skin peptides magainin 2 and PGLa.

The blood stream forms of the malaria parasite *Plasmodium falciparium*, primarily late trophozoites and early schizonts, were assayed by recording the inhibition of the reinvasion of human red cells by the method of Wahlin, B., et al. (1984) Proc. Nat'l Acad. Sci. USA 81, 7912–16, incorporated herein by reference. Quadruplicate microcultures of strain F32 (Tanzania) were incubated for 20 hrs at 37° C. in a complete tissue culture medium, with or without different concentrations of the peptides to be assayed. After acridine orange staining, the percentage of newly infected red cells was scored in a fluorescence microscope. For each culture 40,000 red cells were analysed for parasitic infection. Duplicate assays were run for CA(1–13)M(1–13).

Figure 1:
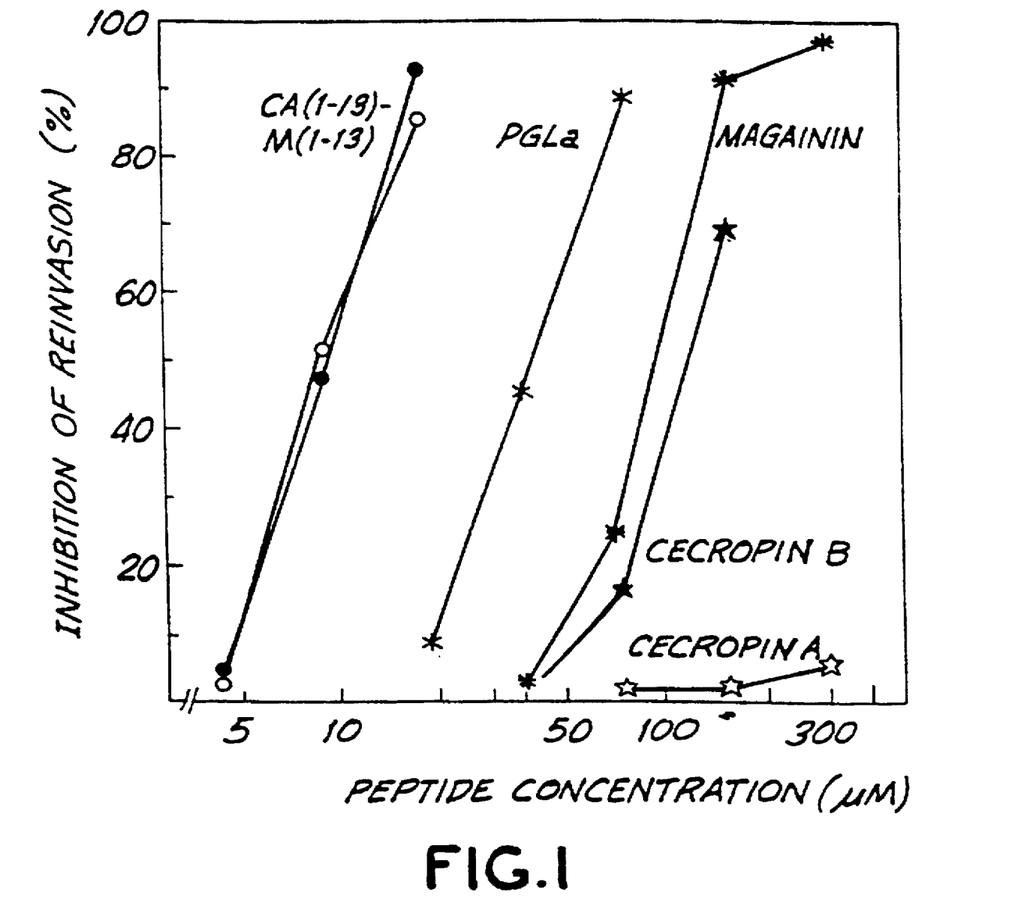
The FIGURE shows peptide concentration ($\mu M$) as a function of inhibition of reinvasion for assays tested for activity against *Plasmodium falciparium*.

FIG. 1 shows the results for CA(1–13)M(1–13), CA, CB, Mag and PGLa. From FIG. 1, CA has only negligible activity; CB is about as potent as Mag; hybrid CA(1–13)M(1–13) is of an order more potent than CB; and, PGLa has intermediate activity. CA(1–18)M(1–18) is even more potent than CA(1–13)M(1–13). CA(1–8)M(1–18) is in fact about four times more potent than CA(1–13)M(1–13): CA(1–8)M(1–18), at a concentration of approximately 2.2 µM yields a 50% inhibition of reinvasion. Only a trace of hemolytic activity was observed with the hybrids of the present invention.

EXAMPLES 9–15 AND COMPARISON WITH CA, CB AND M

Novel peptides CA(1–8)M(1–18), CA(1–9)M(1–17), CB(1–13)M(1–13), CA(1–17)M(1–9), CA(1–18)M(1–8), M(1–13)CA(1–22) and M(1–13)CA(1–13) were prepared as described above (see Examples 1–6). These novel peptides and CA, CB, and M were tested for activity against a variety of organisms selected to represent a number of different types of pathogens, some of them known to be particularly virulent by the inhibition zone assay of Hoffmann et al (1981), Insect Biochem. 11 537–48. As in Examples 1–6, thin agarose plates were prepared with the respective organisms. The diameters of the zones of inhibition were measured after overnight incubation at 30° C. The lethal concentrations were determined as described above (see Examples 1–6; Hultmark et al articles cited thereat). The results of the assays of these novel peptides are shown in Table 3.

As seen from Table 3, the hybrid peptides are less toxic than melittin; and, are more active than at least one of the naturally occurring peptides from which it is derived.

TABLE 1

Cecropin A:

H—Lys—Trp—Lys—Leu—Phe—Lys—Lys—Ile—Glu—Lys—Val—Gly—Gln—Asn—
Ile—Arg—Asp—Gly—Ile—Ile—Lys—Ala—Gly—Pro—Ala—Val—Ala—Val—Val—Gly—
Gln—Ala—Thr—Gln—Ile—Ala—Lys—NH₂ (SEQ ID NO:2)

Cecropin B:

H—Lys—Trp—Lys—Val—Phe—Lys—Lys—Ile—Glu—Lys—Met—Gly—Arg—Asn—
Ile—Arg—Asn—Gly—Ile—Val—Lys—Ala—Gly—Pro—Ala—Ile—Ala—Val—Leu—Gly—
Glu—Ala—Lys—Ala—Leu—NH₂ (SEQ ID NO:3)

Cecropin D:

H—Trp—Asn—Pro—Phe—Lys—Glu—Leu—Glu—Lys—Val—Gly—Gln—Arg—Val—
Arg—Asp—Ala—Val—Ile—Ser—Ala—Gly—Pro—Ala—Val—Ala—Thr—Val—Ala—Gln—
Ala—Thr—Ala—Leu—Ala—Lys—NH₂ (SEQ ID NO:4)

Melittin:

H—Gly—Ile—Gly—Ala—Val—Leu—Lys—Val—Leu—Thr—Thr—Gly—Leu—Pro—
Ala—Leu—Ile—Ser—Trp—Ile—Lys—Arg—Lys—Arg—Gln—Gln(NH₂) (SEQ ID NO:5)

TABLE 2

| PEPTIDE | LETHAL CONCENTRATION IN uM | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| CA(1-37) | 0.2ᵃ | 0.5ᶜ | 1.6ᶜ/2ᵇ | 1ᶜ | 1ᶜ | 4ᵃ | 200ᶜ | 2ᶜ | >200ᵃ | 3ᶜ | 6ᶜ/4ᵇ | >200ᶜ | 60ᶜ | >200ᵃ |
| CD(2-37)* | 3.6ᶜ | 0.6ᶜ | 90ᶜ | 30ᶜ | 12ᶜ | 100ᶜ | | | | | | | | |
| M(1-26) | 0.8ᵃ | | 3ᵃ | | | 0.2ᵃ | 0.3 | 9–50ᶜ | 0.2ᵃ | 0.3ᶜ | 0.5ᵃ | 150ᶜ | 10ᶜ | 4–6ᶜ/4–8ᵇ |
| CA(1-13)M(1-13) | 0.5ᵃ | | 1ᵃ | | | 0.7ᵃ | 0.9 | 4ᶜ | 2ᵃ | 0.6ᶜ | 1ᵃ | 160ᶜ | 20ᶜ | >200ᵃ |
| CA(1-24)M(1-13) | 0.3ᵃ | | 1ᵃ | | | 0.5ᵃ | 1ᶜ | 2ᶜ | 6ᵃ | 0.9ᶜ | 2ᵃ | >200ᶜ | 50ᶜ | >200ᵃ |
| M(16-26)M(1-13) | 0.7ᵃ | | 8ᵃ | | | 0.7ᵃ | 1ᶜ | 30ᶜ | 10ᵃ | 0.8ᶜ | 1ᵃ | 180ᶜ | 25ᶜ | >200ᵃ |
| CA(1-11)CD(12-37)* | 0.5ᶜ | 0.3ᶜ | 1ᶜ | 0.8ᶜ | 0.7ᶜ | 6ᶜ | | | | | | | | |
| CA(25-37)CA(1-13) | 200ᵇ | | 300ᵇ | | | 20ᵇ | | | >300ᵇ | | 20ᵇ | | | >300ᵇ |
| M(1-13)CA(1-13) | 1ᵇ | | 5ᵇ | | | 0.3ᵇ | | | 5ᵇ*** | | 1ᵇ | | | 80? |
| CA(1-8)M(1-12) | 0.4 | | 0.9 | n.d. | | 0.3 | | | 2 | | 0.1 | | | >600 |
| CA(1-8)M(1-10) | 0.5 | | 3 | n.d. | | 0.3 | | | 7 | | 0.8 | | | >600 |
| CA(1-7)M(1-8) | 4 | | 15 | 0.8 | | 1.4 | | | 29 | | 0.7 | | | >200 |
| CA(1-7)M(2-9) | 1 | | 4 | 0.7 | | 0.5 | | | 2 | | 0.5 | | | >600 |
| CA(1-7)M(3-10) | 3 | | 15 | 0.9 | | 6 | | | 200 | | 1 | | | >600 |
| CA(1-7)M(4-11) | 0.6 | | 4 | 0.5 | | 0.6 | | | 8 | | 0.7 | | | >600 |
| CA(1-7)M(5-12) | 0.5 | | 2 | 0.5 | | 0.3 | | | 8 | | 0.4 | | | >500 |
| CA(1-7)M(6-13) | 2 | | 8 | 0.5 | | 1 | | | 51 | | 0.4 | | | >500 |

1. *Escherichia coli* D21
2. *Escherichia coli* D22

TABLE 2-continued

LETHAL CONCENTRATION IN uM

| PEPTIDE | 1 | 2 | 3 | 4 | 5 | 6 | 7 | 8 | 9 | 10 | 11 | 12 | 13 | 14 |
|---|---|---|---|---|---|---|---|---|---|---|---|---|---|---|

3. *Pseudomonas aeruginosa* OT97
4. *Bacillus megaterium* BM11
5. *Micrococcus luteus* Ml11
6. *Bacillus subtilis* Bs11
7. *Bacillus subtilis* Bs11 (Medium E)**
8. *Xenorhabdus nematophilis* Xn21
9. *Staphylococcus aureus* Cowan I
10. *Staphylococcus haemolyticus*
11. *Streptococcus pyogenes*
12. *Candida albicans*
13. *Saccharomyces cerevisiae*
14. Sheep Red Cells

*Using cecropin A numbering.
Values from plates with agar are underlined. In all other cases, the values were determined on agarose plates.
**Vogel and Bonner, J. Biol. Chem. 218: 97–106, 1956
***Indicates flat concentration dependence
$^a$Values obtained after incubation overnight at 30° C. as well as after incubation overnight at 37° C.
$^b$Values obtained after incubation overnight at 30° C.
$^c$Values obtained after incubation overnight at 37° C.

TABLE 3

LETHAL CONCENTRATION IN μM

| Compound | Size (aa) | D21 | OT97 | Bs11 | Bs11 + ME | Staph | Strep | SRC |
|---|---|---|---|---|---|---|---|---|
| CA(1-37) | 37 | 0.2 | 2 | 4 | 200 | 200 | 4 | 200 |
| CB(1-35) | 35 | 0.3 | 1 | nd | nd | 200 | 12 | nd |
| M(1-26) | 26 | 0.8 | 3 | 0.2 | 0.3 | 0.2 | 0.5 | 4–8 |
| CA(1-8)M(1-18) | 26 | 0.3 | 0.7 | 0.4 | 0.5 | 1 | 2 | 600 |
| CA(1-9)M(1-17) | 26 | 0.3 | 1 | 0.7 | 0.9 | 6 | 0.3 | 600 |
| CB(1-13)M(1-13) | 26 | 0.3 | 1 | 0.4 | 0.4 | 4 | 1 | 400 |
| CA(1-17)M(1-9) | 26 | 0.5 | 5 | 0.5 | 1 | 4 | 0.2 | 600 |
| CA(1-18)M(1-8) | 26 | 1 | 15 | 4 | 20 | 600 | 3 | 600 |
| M(1-13)CA(1-22) | 35 | 0.7 | nd | nd | 0.2 | 5* | 1 | 40? |
| M(1-13)CA(1-13) | 26 | 1 | 5 | 0.3 | 0.1 | 5* | 1 | 80? |

D21 = *E. coli*
OT97 = *P. aeruginosa*
Bs11 = *B. subtilis*
Bs11 + ME = *B. subtilis*, plates prepared with medium E
Staph = *S. aureus* Cowan I
Strep = *S. pyogenes*
SRC = Sheep Red Cells
*indicates flat concentration dependence
nd = not determined

TABLE 4

Antimalarial ((*P. falciparum*) activity of natural antibacterial peptides and cecropin A-mellittin hybrids

| Peptide | 50% Reinvasion Inhibition (μM) |
|---|---|
| Cecropin A | n.a. |
| Cecropin B | 110 |
| Cecropin P-1 | 90 |
| Magainin | 80 |
| PGL* | 40 |
| CA(1-13)M(1-13) | 17 |
| CA(1-8)M(1-18) | 4 |
| CA(1-7(M(2-9) | 7.5 |
| CA(1-7)M(5-12) | 9.0 |

EXAMPLE 16

ANTIMICROBIAL TESTING OF GLY-ILE-GLY-LYS-PHE-LEU-LYS-LYS-ALA-LYS-LYS-GLY-ILE-GLY-ALA-VAL-LEU-LYS-VAL-LEU-THR-THR-GLY-LEU

AEROBES

Antimicrobial susceptibility testing was performed using a microdilution broth assay according to the guidelines of the National Committee for Clinical Laboratory Standards (NCCLS) Document M7-A1 (NCCLS. 1990).

Peptide Stock Solutions

The peptide powder as an acetate salt was weighted on an analytical balance and transferred to a polypropylene tube. A solution was prepared at a concentration of 1.024 mg/ml by dissolving the powder in autoclaved (121° C., 20 psi, 20 minutes) deionized water. The peptide solution was used immediately, stored for up to ten days at 4° C., or stored long-term at −70° C. in 1 ml aliquots in polypropylene cryovials.

Broth Medium

Mueller-Hinton broth (MHB) (BBL catalog number 11443) was used in the microtiter plates for diluting the peptide stock solution and for diluting the bacterial inoculum. MBH 5 ml prepared tubes (BBL catalog number 95834) were used to culture an overnight plate of bacteria to the logarithmic phase of growth for inoculating the microtiter plates.

Standardizing Inoculum

Inoculum was prepared by taking a sample of bacteria from a 16-20 hours plate culture and inoculating into 5 ml of (MHB) (BBL catalog number 95834) to an absorbance reading of approximately 0.02 at 600 nm ($Ab_{600}$) on a BECKMAN® DU-64 spectrophotometer. The culture was incubated at 35°-37° C. with shaking (New Brunswick incubator shaker Model G25) and the growth monitored spectrophotometrically until it reached mid-logarithmic phase ($Ab_{600}$ of approximately 0.06). This absorbance represents approximately $1 \times 10^8$ colony-forming units per milliliter (CFUs/ml). The culture was then diluted to approximately $1 \times 10^6$ CFUs/ml in autoclaved MHB (BBL catalog number 11443) to produce the inoculum. A sample of the inoculating culture was diluted in 3 mM phosphate buffer (pH 7.2) through a series of 1:10 dilutions and the $10^{-4}$ and $10^{-5}$ dilutions were plated, incubated overnight at 35°-37° C., and counted the next day to verify inoculum size.

The bacteria used in the antimicrobial susceptibility testing were the quality control reference strains *Staphylococcus aureus* ATCC 29213, *Escherichia coli* ATCC 25922, and *Pseudomonas aeruginosa* ATCC 27853.

Preparation of Microtiter Plate

Microtiter plates (Corning manufacturer number 2585096) were prepared with the use of the BECKMAN® Biomek 1000 (Beckman Instruments, Somerset, N.J.) automated laboratory workstation in combination with manual techniques. The microtiter plate was filled with diluent broth using the Biomek 1000 instrument. Peptide stock solution was manually added to the top drug well of the microtiter plate using a Rainin Pipetman Model P-200. The peptide was serially diluted in two-fold dilutions using the Biomek 1000 instrument. One hundred microliters of the standardized bacterial inoculum was added to every well of the microtiter plates (except the blanks) using an Eppendorf Repeater Model 4780 pipet equipped with an Eppendorf 5 ml combitip (catalog number 22 26 130-4).

Peptides were tested in duplicate. In addition to the test peptide, three standard peptides; a non-treated growth control; and a reference standard of MSI-78 were included to validate the assay. The standard peptides were MSI-500 (gram-negative activity), MSI-63 (gram-positive and gram-negative activity) and MSI-98 (negative control).

The final concentrations of peptide solution in the wells ranged from 0.25 ug/ml to 256 ug/ml. The final concentration of bacteria in the wells was $1-5 \times 10^5$ CFUs/ml. The final volume in the wells was 200 µl.

Incubation

The microtiter plates were incubated overnight (16-20 hours) at 35°-37° C. in a Precision mechanical convection oven incubator Model 30M. Plates were not stacked more than four high.

Reading Results

The Minimum Inhibitory Concentration (MIC), which is defined as the lowest concentration of peptide that completely inhibits growth of the organism was determined using the unaided eye.

The results are shown in Table 5.

TABLE 5

| ORGANISM | NUMBER OF STRAINS | MIC RANGE ug/ml |
|---|---|---|
| S. aureus | 14 | 2–4 |
| s. epidermidis | 12 | 2–4 |
| p. aeruginosa | 13 | 2–32 |
| Group A Streptococcus | 15 | 2–4 |
| Acinetobacter | 12 | 2–4 |
| Xanthomonas | 12 | 2–8 |
| Streptococcus pneumoniae | 11 | 8–16 |

DERMATOPHYTES

Antimicrobial susceptibility testing was performed using a microdilution broth assay as with the aerobes.

Peptide Stock Solutions

Same as for aerobes

Broth Medium

Antibiotic medium 3 (M3) (BBL catalog number 10932) was used in the microtiter plates for diluting the peptide stock solution and for diluting the bacterial inoculum.

Standardizing Inoculum

The dermatophyte cultures were grown on Potato Dextrose Agar for one week. A one centimeter square of growth is teased from the leading edge of the fungus and placed in 2 ml of sterile water in a screw-capped glass tube with glass beads (2 mm) on the bottom. The tubes were vortexed for 20 seconds each and placed in a shaker incubator (New Brunswick incubator shaker Model G25) at 37° C. for 30 minutes. Tubes were removed from the shaker incubator and allowed to settle for 10 minutes. The supernatant was read on a BECKMAN® DU-64 spectrophotometer at 530 nm for percent transmission and adjusted with M3 broth to a transmission of 65%. This culture was then diluted 1:10 in M3 broth for inoculating the microtiter plates.

Preparation of Microtiter Plate

Same as for aerobes

Incubation

The microtiter plates were incubated for 48 hours at 30° C. in a PRECISION® mechanical convection oven incubator Model 4. Plates are never stacked more than four high.

The results are shown in Table 6. *Candida albicans*, a yeast was used for comparison.

TABLE 6

| ORGANISM | MIC |
|---|---|
| T. mentagrophytes ATCC 18748 | 16 |
| T. mentagrophytes ATCC 4808 | 16 |
| T. rubrum ATCC 36262 | 256 |
| C. albicans ATCC 14053 | 64 |

C. ORAL PATHOGEN—PORPHYROMONAS GINGIVALIS

Antimicrobial susceptibility testing was performed using a microdilution broth assay according to the guidelines of the National Committee for Clinical Laboratory Standards (NCCLS) Document M11-T2 (NCCLS, 1989).

Peptide Stock Solutions

Same as for aerobes

Broth Medium

One-half strength Brain Heart Infusion (BHI) (BBL catalog number 11059) supplemented with hemin and menadione is used in the microtiter plates for diluting the peptide stock solution and for diluting the bacterial inoculum.

Standardizing Inoculum

Inoculum is prepared by culturing bacteria from an overnight plate in 5 ml of supplemented BHI. The next day the overnight broth culture is read on a BECKMAN® DU-64 spectrophotometer at 630 nm and diluted with supplemented BHI until an absorbance of 0.02 is reached which represents approximately $1\times10^6$ colony-forming units per milliliter (CFUs/ml). This culture is used to inoculate the microtiter plates. A sample of the inoculating culture is diluted in supplemented BHI through a series of 1:10 dilutions and the $10^{-5}$ and $10^{-6}$ dilutions are plated, incubated 48 hours at 35°–37° C. anaerobically, and counted to verify inoculum size.

Preparation of Microtiter Plate

Same as for aerobes

Incubation

The microtiter plates are incubated anaerobically for 48 hours at 35°–37° C. in a COY® anaerobic chamber Type A. Plates are never stacked more than four high.

The results are shown in Table 7. *E. coli* ATCC 25922 was used as a standard.

TABLE 7

| ORGANISM P. GINGIVALIS STRAIN | MIC (µg/ml) |
|---|---|
| 381 | 64 |
| A7A1-28 | 32 |
| ESO-127 | 4–8 |
| FAY-19M-1 | 16 |
| 9-14K-1 | 16 |
| VAG-4 | 32 |
| W-50 | 32 |
| 2561 | 16 |
| VAG-1 | 64 |
| ATCC 33277 | 64–128 |
| *E. coli* ATCC 25922 | 8 |

---

What is claimed is:

1. A hybrid peptide or a pharmaceutically acceptable salt thereof which consists of:
    a hydrophobic sequence of seven to twenty-six amino acids corresponding to a sequence on a naturally occurring peptide selected from the group consisting of cecropin A (CA), procecropin A (proCA), cecropin B (CB), cecropin D (CD), melittin (M), and magainin (Mag); and
    a hydrophilic sequence of eight to twenty-four amino acids corresponding to another of said naturally occurring peptides.

2. A hybrid peptide of claim 1 which is CA(1–13)M(1–13) or a pharmaceutically acceptable salt thereof.

3. A hybrid peptide of claim 1 which is CA(1–24)M(1–13) or a pharmaceutically acceptable salt thereof.

4. A hybrid peptide of claim 1 which is CA(1–11)CD(12–37) or a pharmaceutically acceptable salt thereof.

5. A hybrid peptide of claim 1 which is CA(1–8)M(1–12) or a pharmaceutically acceptable salt thereof.

6. A hybrid peptide of claim 1 which is CA(1–7)M(2–9) or a pharmaceutically acceptable salt thereof.

7. A hybrid peptide or a pharmaceutically acceptable salt thereof which consists of:
    a hydrophobic sequence of seven to twenty-six amino acids corresponding to one of an amino terminal sequence or a carboxyl terminal sequence on a naturally occurring peptide selected from the group consisting of cecropin A, procecropin A (proCA), cecropin B (CB), cecropin D (CD), melittin (M), and magainin (Mag); and
    a hydrophilic sequence of eight to twenty-four amino acids corresponding to the other of an amino terminal sequence or a carboxyl terminal sequence of the same naturally ocurring peptide, wherein the amino terminal sequence of said naturally occurring peptide corresponds to the carboxyl terminal sequence of said hybrid peptide, and the carboxyl terminal sequence of said naturally occurring peptide corresponds to the amino terminal sequence of said hybrid peptide.

8. A hybrid peptide of claim 7 which is M(16–26)M(1–13) or a pharmaceutically acceptable salt thereof.

9. A pharmaceutical composition containing a pharmaceutically acceptable carrier together with an antibiotically effective amount of the hybrid peptide of claim 1.

10. A composition of claim 9 wherein the hybrid peptide is CA(1–13)M(1–13) or a pharmaceutically acceptable salt thereof.

11. A composition of claim 9 wherein the hybrid peptide is CA(1–24)M(1–13) or a pharmaceutically acceptable salt thereof.

12. A composition of claim 9 wherein the hybrid peptide is CA(1–11)CD(12–37) or a pharmaceutically acceptable salt thereof.

13. A composition of claim 9 wherein the hybrid peptide is CA(1–8)M(1–12) or a pharmaceutically acceptable salt thereof.

14. A composition of claim 9 wherein the hybrid peptide is CA(1–7)M(2–9) or a pharmaceutically acceptable salt thereof.

15. A pharmaceutical composition containing a pharmaceutically acceptable carrier together with an antibiotically effective amount of the hybrid peptide of claim 7.

16. A composition of claim 15 wherein the hybrid peptide is M(16–26)M(1–13) or a pharmaceutically acceptable salt thereof.

17. A method of treating a patient in need of treatment for a microbial infection comprising administering to said patient an antimicrobially effective amount of the hybrid peptide of claim 1.

18. The method of claim 17 wherein the hybrid peptide comprises CA(1–13)M(1–13), CA(1–8)M(1–18) or a pharmaceutically acceptable salt thereof.

19. A method of treating a patient in need of treatment for a microbial infection comprising administering to said patient an antimicrobially effective amount of the hybrid peptide of claim 7.

20. A hybrid peptide selected from the group consisting of
CA(1–13)Mag(13–23)
M(15–26)Mag(13–23)
Mag(13–23)CA(1–13)
Mag(13–23)M(15–26)
M(1–13)CB(1–13)
M(1–12)ProCA(1–13)
M(1–15)C(1–11)
M(16–26)CA(14–37)
CA(25–36)ProCA(1–13)
CA(25–37)CA(1–13)
CA(1–24)M(1–13)
CA(1–13)M(1–13)
M(16–26)M(1–13)
M(16–26)CA(23–37)
CA(1–24)M(16–26)
CB(25–35)M(14–26)
CA(1–17)CD(12–37)
CA(1–8)M(1–18)
CA(1–9)M(1–17)
CB(1–13)M(1–13)
CA(1–17)M(1–9)
CA(1–18)M(1–8)
M(1–13)CA(1–22)
M(1–13)CA(1–13)
CA(1–8)M(1–12)
CA(1–8)M(1–10)
CA(1–7)M(1–8)
CA(1–7)M(2–9)
CA(1–7)M(3–10)
CA(1–7)M(4–11)
CA(1–7)M(6–13).

21. A pharmaceutical composition containing a pharmaceutically acceptable carrier together with an antibiotically effective mount of the hybrid peptide of claim 20.

22. A method of treating a patient in need of treatment for a microbial infection comprising administering to said patient an antimicrobially effective amount of the hybrid peptide of claim 20.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: YES     ( v ) FRAGMENT TYPE: N-terminal     ( x i ) SEQUENCE DESCRIPTION: SEQ ID NO:1:

```
Gly Ile Gly Lys Phe Leu Lys Lys Ala Lys Lys Gly Ile Gly Ala Val
 1               5                  10                  15

Leu Lys Val Leu Thr Thr Gly Leu
                20
```

( 2 ) INFORMATION FOR SEQ ID NO:2:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: YES     ( v ) FRAGMENT TYPE: N-terminal     ( x i ) SEQUENCE DESCRIPTION: SEQ ID NO:2:

-continued

```
Lys  Trp  Lys  Leu  Phe  Lys  Lys  Ile  Glu  Lys  Val  Gly  Gln  Asn  Ile  Arg
 1              5                        10                            15

Asp  Gly  Ile  Ile  Lys  Ala  Gly  Pro  Ala  Val  Ala  Val  Val  Gly  Gln  Ala
               20                       25                       30

Thr  Gln  Ile  Ala  Lys
               35
```

( 2 ) INFORMATION FOR SEQ ID NO:3:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: YES     ( v ) FRAGMENT TYPE: N-terminal     ( x i ) SEQUENCE DESCRIPTION: SEQ ID NO:3:

```
Lys  Trp  Lys  Val  Phe  Lys  Lys  Ile  Glu  Lys  Met  Gly  Arg  Asn  Ile  Arg
 1              5                        10                            15

Asn  Gly  Ile  Val  Lys  Ala  Gly  Pro  Ala  Ile  Ala  Val  Leu  Gly  Glu  Ala
               20                       25                       30

Lys  Ala  Leu
          35
```

( 2 ) INFORMATION FOR SEQ ID NO:4:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: YES     ( v ) FRAGMENT TYPE: N-terminal     ( x i ) SEQUENCE DESCRIPTION: SEQ ID NO:4:

```
Trp  Asn  Pro  Phe  Lys  Glu  Leu  Glu  Lys  Val  Gly  Gln  Arg  Val  Arg  Asp
 1              5                        10                            15

Ala  Val  Ile  Ser  Ala  Gly  Pro  Ala  Val  Ala  Thr  Val  Ala  Gln  Ala  Thr
               20                       25                       30

Ala  Leu  Ala  Lys
          35
```

( 2 ) INFORMATION FOR SEQ ID NO:5:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: YES     ( v ) FRAGMENT TYPE: N-terminal     ( x i ) SEQUENCE DESCRIPTION: SEQ ID NO:5:

```
Gly  Ile  Gly  Ala  Val  Leu  Lys  Val  Leu  Thr  Thr  Gly  Leu  Pro  Ala  Leu
```

```
  1                 5                      1 0                         1 5
Ile Ser Trp Ile Lys Arg Lys Arg Gln Gln
                2 0                 2 5
```